(12) United States Patent
Layzell et al.

(10) Patent No.: US 6,220,076 B1  
(45) Date of Patent: Apr. 24, 2001

(54) DIFFERENTIAL GAS ANALYZER

(75) Inventors: David B. Layzell, Kingston; Stephen Hunt, Glenburnie; Adrian N. Dowling, Kingston; Roy A. Young, Odessa, all of (CA)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 09/306,431

(22) Filed: May 6, 1999

(51) Int. Cl.$^7$ .................................................. G01N 27/00
(52) U.S. Cl. ............................................. 73/23.2; 73/23.21
(58) Field of Search .................................. 73/23.2, 23.21, 73/23.3, 23.31

(56) References Cited

U.S. PATENT DOCUMENTS

| | | | |
|---|---|---|---|
| 3,300,282 | | 1/1967 | Risk et al. . |
| 3,585,842 | | 6/1971 | Roof . |
| 3,647,392 | * | 3/1972 | McGinnis ............................ 23/254 E |
| 3,963,927 | * | 6/1976 | Bruce et al. ........................ 250/338 |
| 4,233,033 | * | 11/1980 | Eifler et al. ........................ 23/232 E |
| 4,410,632 | * | 10/1983 | Dilley et al. .......................... 436/20 |
| 5,065,613 | * | 11/1991 | Lehnert et al. ....................... 73/23.2 |
| 5,072,737 | * | 12/1991 | Goulding ............................. 128/718 |
| 5,243,408 | * | 9/1993 | Whitman, III ....................... 356/430 |
| 5,270,009 | * | 12/1993 | Nakamori et al. ..................... 422/83 |
| 5,542,284 | * | 8/1996 | Layzell et al. ........................ 73/23.2 |
| 5,616,850 | * | 4/1997 | Sage ................................. 73/23.31 |
| 5,629,473 | * | 5/1997 | Hayami .............................. 73/23.31 |
| 5,780,715 | * | 7/1998 | Imblum ............................... 73/23.21 |
| 5,804,703 | * | 9/1998 | Wind et al. ......................... 73/25.01 |
| 5,830,412 | * | 11/1998 | Kimura et al. ........................ 422/90 |
| 5,849,175 | * | 12/1998 | Dietz et al. ....................... 205/784.5 |
| 5,983,876 | * | 11/1999 | Irons et al. ........................... 123/676 |
| 6,076,392 | * | 6/2000 | Drzewiecki ........................... 73/23.2 |
| 6,079,251 | * | 6/2000 | Gaultier et al. ..................... 73/23.31 |

FOREIGN PATENT DOCUMENTS

| | | | |
|---|---|---|---|
| 1 225 075 | * | 3/1971 | (GB) . |
| 2 018 426 | * | 4/1979 | (GB) . |
| 7912056 | | 4/1979 | (GB) . |
| 58-203188 | | 10/1983 | (JP) . |
| 60-93953 | * | 5/1985 | (JP) . |

OTHER PUBLICATIONS

J.R. Willms, A.N. Dowling, Z.M. Dong, S. Hunt, B.J. Shelp, D.B. Layzell, "The simultaneous measurement of low rates of CO2 and O2 exchange in biological systems", 1977, Analytical Biochemistry 254, 272–282.*

Willms, J.R., et al. "The Simultaneous Measurement of Low Rates of $CO_2$ and $O_2$ Exchange in Biological Systems." *Analytical Biochem.* 254:272–282 (1997).

* cited by examiner

*Primary Examiner*—Hezron Williams  
*Assistant Examiner*—Charles D Garber  
(74) *Attorney, Agent, or Firm*—Stephen J. Scribner; Carol Miernicki Steeg; Richard J. Hicks

(57) ABSTRACT

A method and apparatus for measuring differential and absolute concentrations of a selected gas, preferably oxygen, in two flowing gas streams is described. A reference gas and a sample gas in separate gas flow paths are passed at selected temperature, pressure and flow rate over a pair of gas sensors, connected in series with their cathodes or anodes connected together, which produce output signals proportional to the differential selected gas concentration between the sensors and the absolute selected gas pressure in each sensor. The output signals may be amplified and recorded by any conventional means.

4 Claims, 2 Drawing Sheets

DIFFERENTIAL GAS ANALYZER

FIELD OF THE INVENTION

This invention relates to an instrument for measuring the difference in concentration of a selected gas, such as $O_2$, between two flowing gas streams, and use of the instrument to measure the rate of production or consumption of a selected gas from living or non-living materials. This invention also contemplates measurement of absolute concentrations of a selected gas in each of the flowing gas streams.

BACKGROUND OF THE INVENTION

Many industrial, medical, biological, and research situations require measurements of concentrations of selected gases in flowing gas streams. Such measurements may comprise determining the absolute concentration of a selected gas in a flowing gas stream, or the difference in concentration of a selected gas between two flowing gas streams. The latter is typically employed in research and biological applications where, for example, quantification of the $O_2$ consumption or production by biological material is required. Measurements involve placing biological material in a cuvette containing a known concentration of $O_2$, and monitoring changes in the atmosphere within the cuvette with time. Preferably, an open gas exchange system is employed, which involves placing the biological material in a cuvette through which gas of known composition flows at a measured rate. The $O_2$ concentration of the effluent gas from the cuvette is monitored by an $O_2$ analyzer, and the difference in $O_2$ concentration between the input and effluent gases multiplied by the flow rate through the cuvette gives a measure of the rate of $O_2$ exchange. If the $O_2$ analyzer used in the open system is itself a flow-through instrument, the $O_2$ concentration in the effluent gas stream can be monitored continuously, and real-time measurements of $O_2$ exchange can be performed.

The most accurate method of measuring $O_2$ exchange in an open flow gas exchange system is to use a differential $O_2$ analyzer. Such instruments continuously monitor the difference in $O_2$ concentration between a reference gas stream and a branch of the reference gas stream which has passed through a cuvette containing the biological material under study. Where large oxygen differentials between the reference and sample gas streams occur, sensitivity of the differential analyzer is not critical and instruments such as those containing either paramagnetic $O_2$ sensors (e.g. the Oxygor™ 6N, Maihak AG, Hamburg, Germany) or zirconium oxide sensors (e.g. Model S-3A/II, Servomex Company, MA 02062, USA) may be used. The sensitivities of these instruments are limited; the Oxygor 6N can resolve a minimum $O_2$ differential of only 100 ppm $O_2$ when air is used as the reference gas, and under the same conditions the Servomex S-3A/II has an accuracy limit of only ±30 ppm $O_2$ in differential mode (note that 1 $PaO_2$ is approximately equivalent to 10 ppm $O_2$). However, neither instrument has the sensitivity required to measure very small $O_2$ differentials (e.g., less than 10 ppm) that occur when the biological material under study has a low metabolic rate, or the sample is very small. Also, both types of differential $O_2$ analyzer are essentially laboratory-based intents which are not readily adaptable for field use, as each requires AC power and stable environmental conditions for most accurate function. They also require calibration by laboratory-based calibration systems involving compressed gases and/or gas mixing instruments. This adds to the considerable expense of the analyzers.

The differential $O_2$ analyzer described in our U.S. Pat. No. 5,542,284, issued Aug. 6, 1996, was developed to overcome the sensitivity limitations of the above-mentioned analyzers. Using $O_2$ sensors, which are $O_2$ cells that operate on the principle of a lead-oxygen battery, the prior device permits measurement of as little as 2 ppm differential in $O_2$ concentration between two flowing gas streams that contain 21% $O_2$ (210,000 ppm). While the prior analyzer provides for measurement of very small differentials in $O_2$ concentration, it has other limitations. For example, it is not possible to obtain an absolute measurement of the $O_2$ concentration in either of the sample and reference gas steams. Since many applications require information about the absolute $O_2$ concentration in the gas streams, this is a drawback of the prior design.

OBJECT OF THE INVENTION

It is an object of the present invention to overcome the limitations of the prior art outlined above by providing an inexpensive differential gas analyzer, adaptable for use in the laboratory or in the field, that is capable of continuously measuring differential and absolute concentrations of a selected gas in reference and sample flowing gas streams containing any partial pressure of the selected gas, and capable of resolving differentials of less than 0.5 Pa in a background range from about 10 Pa to about 100 kPa of the selected gas.

SUMMARY OF THE INVENTION

According to a broad aspect, the present invention relates to an apparatus for measuring the differential in concentration of a selected gas between a first flowing gas stream and a second flowing gas stream, comprising: first and second sensors for the selected gas respectively disposed in the first and second flowing gas streams, the gas sensors being connected to each other in series with electrodes of same polarity connected; and means for amplifying a differential signal produced across both of the sensors; wherein the differential signal is indicative of the differential in concentration of the selected gas. Preferably, the electrodes of same polarity are cathodes. According to a preferred embodiment of the invention, the apparatus further comprises means for applying a voltage to the amplifier means to offset the differential signal without affecting a calibrated gain setting. Also according to a preferred embodiment of the invention, the selected gas is oxygen.

An apparatus in accordance with the invention further comprises at least one amplifier connected to a said sensor, the amplifier providing a signal proportional to absolute concentration of the selected gas in the flowing gas stream corresponding to the sensor. In accordance with a preferred embodiment, the apparatus comprises first and second amplifiers respectively connected to the first and second sensors, to obtain signals proportional to absolute concentrations of the selected gas in each of the first and second flowing gas streams.

According to another aspect of the invention, there is provided a method for measuring the differential in concentration of a selected gas between a first flowing gas stream and a second flowing gas stream, comprising: respectively disposing first and second sensors for the selected gas in the first and second flowing gas streams, the gas sensors being connected in series with electrodes of same polarity connected; and amplifying a differential signal produced across both of the sensors; wherein the differential signal is indicative of the differential concentration of the selected gas.

In accordance with yet another aspect of the invention, there is provided a method for measuring the absolute concentration of a selected gas in a first flowing gas stream and in a second flowing gas stream, comprising: respectively disposing first and second sensors for the selected gas in the first and second flowing gas streams, the gas sensors being connected in series with electrodes of same polarity connected; and amplifying a signal produced across each of the first and second sensors; wherein the signal across the first sensor is proportional to the absolute concentration of the selected gas in the first flowing gas stream, and the signal across the second sensor is proportional to the absolute concentration of the selected gas in the second flowing gas stream.

In a preferred embodiment of the invention, the method further comprises measuring the differential in concentration of the selected gas between the first flowing gas stream and the second flowing gas stream, wherein the differential in concentration is obtained by amplifying a differential signal produced across both of the sensors.

In another embodiment of the invention, the method further comprises measuring the differential in concentration of the selected gas between the first flowing gas stream and the second flowing gas stream, wherein the differential in concentration is obtained by calculating a difference between the signal produced the first sensor and the signal produced across the second sensor.

BRIEF DESCRIPTION OF THE DRAWINGS

Embodiments of the invention will now be described, by way of example, with reference to the accompanying drawings, wherein.

DETAILED DESCRIPTION OF THE INVENTION

According to a broad aspect, the invention relates to a gas analyzer for continuously measuring differential concentrations of a selected gas between a reference flowing gas stream and a sample flowing gas stream, each containing any partial pressure of the selected gas. A gas analyzer according to the invention also provides for absolute measures of a selected gas in either or both of the sample and reference gas streams.

A differential gas analyzer according to the invention employs a gas sensor in each of the reference and sample gas streams. The gas sensors can be any commercially available sensors designed to detect a selected gas, such as oxygen, hydrogen, or a toxic gas, so long as the sensors produce a current or voltage having a magnitude related to the concentration of the selected gas to which they are exposed. While the preferred embodiment of the present invention is based on the sensors producing a voltage (i.e., voltage sources), sensors that are current sources may also be employed according to the invention, as current sources can be converted to voltage sources by connecting a shunt resistance across the output terminals, as is well known in the art. Also in accordance with the invention, the sensors can be a combination of a voltage source sensor and a current source sensor.

According to a preferred embodiment of the invention, the gas analyzer is a differential oxygen analyzer. Such an oxygen analyzer can be used in any situation where concentrations of oxygen are perturbed and measures of such perturbations are required. Perturbations may result from exposure of an oxygen-containing gas to biological materials, as well as to various non-biological materials. Examples of biological materials include bacterial, yeast, cell, and tissue cultures, portions of organisms, and entire organisms.

Figure 1:
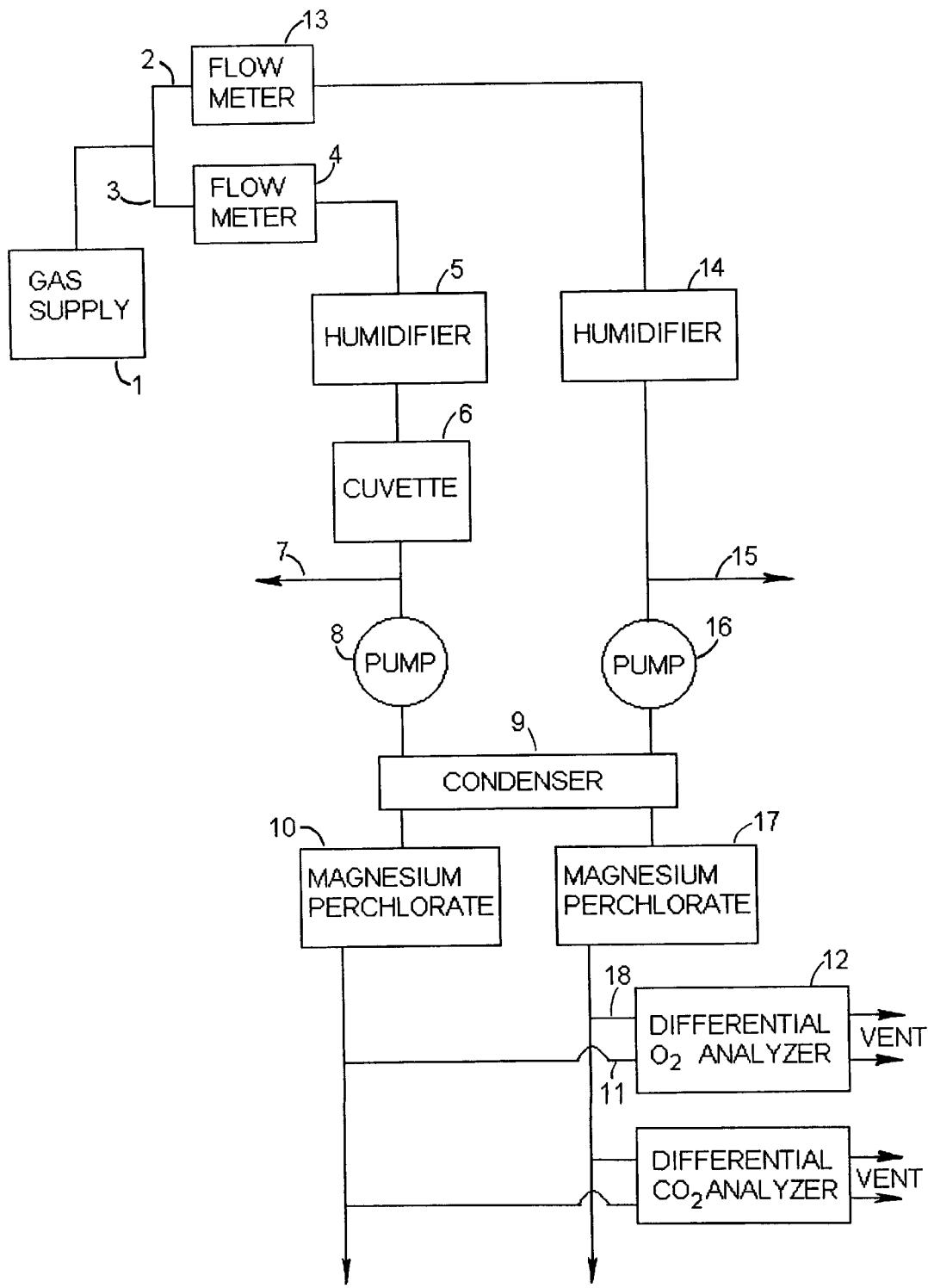
FIG. 1 is a block diagram showing an example of a typical arrangement of a differential oxygen analyzer according to the present invention.

Use of a differential oxygen analyzer according to the invention, including connection of sample and reference gas streams, calibration, and the like, is described in detail in our U.S. Pat. No. 5,542,284, issued Aug. 6, 1996, the contents of which are incorporated herein by reference. FIG. 1 is an example of a typical configuration of a differential gas analyzer according to the invention which employs a supply of gas 1 (air or a mixed gas) containing $O_2$ which is divided into a reference stream 2 and a sample stream 3. The flow rate of the sample stream is measured using a flow meter 4, and the gas passes through a humidification system 5 before entering a cuvette 6 containing biological material (for example) which either produces or consumes $O_2$. After passage through the cuvette, a proportion of the gas is passed through a vent 7 to the atmosphere, and the remainder is dried by being drawn, by a pump 8, through a condenser in an ice water bath 9 and through a column of magnesium perchlorate 10. The gas then enters the sample side 11 of the differential $O_2$ analyzer 12.

The flow rate of the reference gas stream is measured by a flow meter 13 and the gas then enters a humidifier 14 of the same type as that employed for the sample gas stream. A proportion of the reference gas is passed through a vent 15 to the atmosphere, and the remainder is dried by being drawn, by a pump 16, through a condenser in an ice water bath 9 and through a magnesium perchlorate column 17. The reference gas then enters the reference side 18 of the $O_2$ analyzer. After passage through the analyzer, both the reference and sample gas streams are vented to atmosphere. It will be apparent to those skilled in the art that the arrangement shown in FIG. 1 is only an example of a configuration and many others are possible, each customized to suit specific applications.

The preferred embodiment employs $O_2$ sensors (e.g., model KE-25, Figaro USA Inc., IL; model GPR-11-37-1, Analytical Industries Inc., Pomona, Calif.), which are $O_2$ cells that operate on the principle of a lead-oxygen battery. Each sensor contains a lead anode, an oxygen cathode (which is made of gold) and a weak acid electrolyte. $O_2$ passing across the surface of the sensor diffuses through a Teflon™ FEP membrane and is reduced electrochemically at the gold electrode. As supplied from the manufacturer, each sensor contains a resistor and a thermistor connected in series (with a total resistance of about 1.2 kΩ) between the anode and the cathode so that a voltage differential produced by the cell is proportional to the $O_2$ concentration at the Teflon™ membrane despite variations in temperature.

Figure 2:
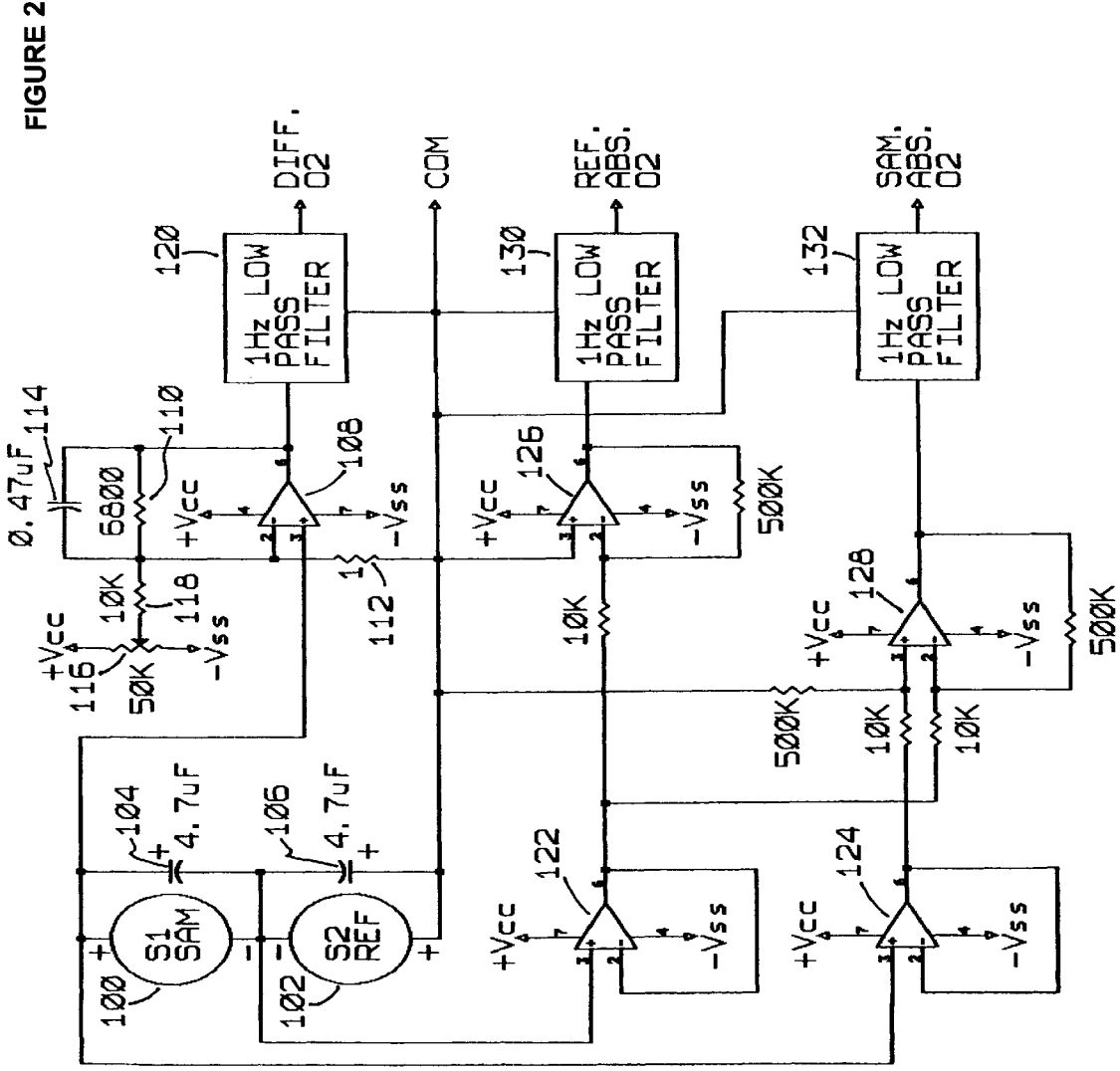
FIG. 2 is an electrical schematic diagram of a differential oxygen analyzer circuit according to a preferred embodiment of the present invention.

A differential $O_2$ analyzer circuit of the preferred embodiment is capable of resolving $O_2$ differentials of less than 0.5 Pa in a background range from about 10 Pa to about 100 kPa of $O_2$ (note that 1 $PaO_2$ is approximately equivalent to 10 ppm $O_2$). Referring to FIG. 2, the preferred embodiment employs sample 100 and reference 102 $O_2$ sensors (GPR-11-37-1, Analytical Industries Inc., Pomona, Calif.) identified as S1 SAM and S2 REF, respectively. The $O_2$ sensors are connected in series with their cathodes connected together. The reference sensor 102 has its anode connected to circuit common. A 4.7 $\mu$F capacitor 104, 106 is connected across each sensor to reduce noise before any signals are amplified. A differential oxygen signal is derived from the total voltage produced across both sensors and amplified via a non-inverting amplifier 108 with a gain of 6800. Preferably, a low noise, chopper stabilized operational amplifier such as the LTC1150 (Linear Technology Corp., Milpitas, Calif.) is employed. The gain is set by a 6.8 k$\Omega$ feedback resistor 110 and a 1$\Omega$ resistor 112 connected to the circuit common, as is well known in the art. It is preferred that temperature-stable precision resistors, such as metal film resistors, are employed. A 0.47 $\mu$F capacitor 114 across the 6.8 k$\Omega$ feedback resistor 110 prevents any high frequency noise from being amplified. A 50 k$\Omega$ potentiometer 116 connected between Vcc and Vss has a 10 k$\Omega$ resistor 118 connected between its wiper and the negative input terminal of the amplifier, which allows zeroing of the output of the amplifier. This compensates for small differences in each of the sensor outputs as they age or react differently to environmental conditions and provides a capability to offset the differential oxygen signal without affecting calibrated gain settings. Other resistances can be substituted for the 10 k$\Omega$ resistor 118, to provide the necessary offset for a given situation. For example, in applications where very large $O_2$ differentials are to be measured, decreasing the value of resistor 118 appropriately will provide a greater range of offset so as to prevent saturation of the differential voltage signal. The output of the differential oxygen amplifier is passed through a 1 Hz low pass filter 120 to further reduce any high frequency components of the signal.

The remaining circuitry of the preferred embodiment isolates the signals from each of the two sensors 100, 102 to give absolute oxygen readings from the reference gas sensor 102 and from the sample gas sensor 100, should such be desired. High impedance unity gain buffers 122, 124 are used to follow each of the sensors' voltages to minimize the amount of noise introduced into the differential oxygen signal amplifier 108. The voltage signal across the reference sensor 102 is negative with respect to ground and is amplified after the buffer 122 by an inverting amplifier 126. The voltage signal across the sample sensor 100 is superimposed on the reference sensor voltage and a non-inverting differential amplifier 128 is used to amplify only the output of the sample sensor. Both the reference and sample signals are positive with respect to ground and each is passed through a 1 Hz low pass filter 130, 132 to further reduce any high frequency components of the signals. In other embodiments of the invention in which absolute measurements from only one of either the sample or reference sensors is desired, only one buffer and inverting or non-inverting amplifier, as the case may be, are employed.

The differential signal, and/or either or both of the absolute sample and reference signals, can be fed a suitable recording device, such as a plotter, or analogue-to-digital (A-D) converter, and computer, for recording, data storage and manipulation, and the like. An A-D convertor may be provided as part of the analyzer, or it may be a discrete device, or part of a computer such as a personal computer. A differential oxygen analyzer in accordance with the invention can be used in conjunction with a $CO_2$ analyzer to measure respiratory quotient (RQ) of biological material, as well as photosynthetic quotient (PQ) of photosynthetic biological material, as known in the art and described in detail in U.S. Pat. No. 5,542,284.

As discussed below, the sensors 100,102 used in the preferred embodiment have built-in temperature compensation, such that each sensor's output signal is relatively stable with respect to temperature fluctuations. Nevertheless, to achieve greater temperature stability, it is preferred that the sensors and the circuitry are disposed on, and even enclosed by, a substrate or casing having a high thermal mass, so as to maintain a somewhat constant temperature of the components. If desired, the substrate or casing is heated or cooled to a constant temperature by any suitable heating or cooling apparatus, such as electrical heating or cooling elements, or by providing a water jacket with temperature-controlled water circulated therethrough. As an alternative to any of these exemplary means for achieving greater temperature stability, the ambient temperature in the immediate vicinity of the sensors and circuitry can be monitored, and the data used to correct measurements of $O_2$ concentration.

The preferred embodiment has been optimized for measuring very small differentials in oxygen concentration between two flowing gas streams, e.g., differentials on the order of 0.5 Pa or less. As this minute $O_2$ differential corresponds to very small voltage differentials being produced by the $O_2$ sensors, the voltage signals are vulnerable to noise. Accordingly, the preferred embodiment employs circuit components to reduce this noise, such as the 4.7 $\mu$F capacitors 104, 106 connected across the sensors, and the 0.47 $\mu$F capacitor 114 connected across the 6.8 k$\Omega$ feedback resistor 110. It will be appreciated by those skilled in the art that other values of these capacitors can be employed in other applications to reduce noise as required. In some applications where noise is not critical, such as where large $O_2$ differentials are to be measured, the sensor capacitors 104, 106 and/or the feedback capacitor 114 can be eliminated. Further, noise can also be reduced, with or without the inclusion of any or all of these capacitors, by disposing the sensors and the circuit in a Faraday cage or the like.

In some embodiments, as an alternative to the compensation voltage supplied by the 50 k$\Omega$ potentiometer 116 and Vcc and Vss, a potentiometer is connected in parallel across one of the sensors, with the wiper of the potentiometer connected to the input of the amplifier. For such an arrangement not to affect the calibration of the analyzer, the potentiometer is connected across the reference sensor 102. Further, in situations where large $O_2$ differentials are to be measured, the compensation voltage can be eliminated completely, as any small differences in each of the sensor outputs will not substantially affected the differential voltage signal.

In the preferred embodiment shown in FIG. 2, the cathodes of the two $O_2$ sensors are connected together. In an alternative embodiment, the two gas sensors have their anodes connected together in a similar configuration, which simply changes the polarity of the resulting differential and absolute voltage outputs.

In yet another alternative embodiment, the reference sensor is calibrated with small differential gas signals, in which case the resulting negative differential voltage output is indicative of that differential gas signal. Accordingly, it is apparent that either sensor can be calibrated and used as the sample sensor, with the other sensor functioning as the reference sensor.

The preferred embodiment of the present invention provides at least four advantages over our differential gas analyzer described in U.S. Pat. No. 5,542,284, issued Aug. 6, 1996. Firstly, the prior circuit requires that the $O_2$ sensors used are current devices; however, virtually all commercially available $O_2$ sensors are supplied by the manufacturer as voltage devices. In constructing an analyzer in accordance with the prior design, the $O_2$ sensors must be modified by removing internal resistors within the cells, which increases manufacturing costs. In contrast, an analyzer in accordance with the present invention uses intact cells, thereby saving manufacturing costs. The circuit of the present invention makes it easier to troubleshoot the analyzer and identify a defective or spent $O_2$ sensor. Also, by using "off the shelf" $O_2$ sensors, the sensors, which have a limited life span, are easily replaced by any user.

Secondly, the internal resistors of the $O_2$ sensors are part of a temperature correction circuit which prevents drift of the sensor output voltage with temperature, at a given $O_2$ concentration. Removing the internal resistors of the sensors, as required in the prior design, effectively destroys the temperature correction circuitry. As a result, the prior design employs a temperature-controlled sensor block into which the sensors are embedded, to ensure that they remain at a constant temperature. The provision of the temperature controlled sensor block for the modified $O_2$ sensors adds to the complexity of the prior design and increases the cost of manufacturing. In contrast, the preferred embodiment of the present invention employs intact sensors with built in temperature compensation, eliminating need for a temperature-controlled sensor block and the associated complexity and cost.

Thirdly, as mentioned above, the prior design does not provide outputs of the two $O_2$ sensors, so that absolute measures of the concentration of $O_2$ in either or both of the reference and sample gas streams cannot be obtained. To obtain information about the absolute $O_2$ concentration in the gas streams, it is necessary to include another $O_2$ sensor in one of the gas streams (typically the reference gas stream). This adds to the cost of the analyzer and, because $O_2$ sensors consume $O_2$, the inclusion of an additional sensor in one of the gas streams could potentially alter the $O_2$ concentration in the gas stream. In applications where small concentrations, or changes in concentrations, of $O_2$ are being measured, this could potentially reduce the accuracy of the measurements. In contrast, the present invention provides for separate measurements of the reference and sample gas streams, in addition to, and simultaneously with, measurement of the differential $O_2$ concentration. The present invention therefore eliminates the need for additional absolute sensors, and the cost thereof. This also eliminates any concern about $O_2$ consumption by the sensors interfering with the measurements.

A further advantage of the present invention is the increased dynamic range of the analyzer, relative to the previous design. That is, under certain situations the $O_2$ differential may be so large that it saturates the output of the differential signal. According to the invention, a differential signal could be calculated from the two absolute $O_2$ measurements obtained from the sample and reference gas streams.

It will be appreciated that the present invention is not limited to use with gas exchange systems such as the differential gas analyzers discussed above and the differential oxygen analyzer of the preferred embodiment. That is, the invention can easily be configured for compatibility with other types of sensors used in applications where differential measurements are required, such as, for example, in differential temperature and pressure analysis systems. The only requirement is that the sensors produce a voltage or current having a magnitude that is related to the magnitude of the variable being measured. Suitable environmental condition sensors (e.g., pressure, force, airflow, temperature, and humidity) are available from Honeywell (USA), and load cells are available from Rice Lake Weighing Systems (USA). Of course, for some of these sensors it is necessary to provide simple additional biasing circuitry.

Those skilled in the art will recognize, or be able to ascertain through routine experimentation, equivalents to the preferred embodiment described herein. Such equivalents are considered to be within the scope of the invention and are covered by the appended claims.

We claim:

1. An apparatus for measuring the differential in concentration of a selected gas between a first flowing gas stream and a second flowing gas stream, comprising:

first and second sensors for said selected gas respectively disposed in the first and second flowing gas streams, the gas sensors being connected to each other in series with electrodes of same polarity connected;

means for amplifying a differential signal produced across both of said sensors, the differential signal indicative of the differential in concentration of said selected gas; and at least one amplifier connected to a said sensor, said amplifier providing a signal proportional to absolute concentration of the selected gas in the flowing gas stream corresponding to said sensor.

2. The apparatus of claim 1, wherein first and second amplifiers are respectively connected to said first and second sensors, to obtain signals proportional to absolute concentrations of the selected gas in each of said first and second flowing gas streams.

3. A method for measuring the differential in concentration of a selected gas between a first flowing gas stream and a second flowing gas stream, comprising:

respectively disposing first and second sensors for said selected gas in the first and second flowing gas streams, the gas sensors being connected in series with electrodes of same polarity connected;

amplifying a differential signal produced across both of said sensors, the differential signal being indicative of the differential concentration of said selected gas; and providing at least one amplifier connected to a said sensor, said amplifier providing a signal proportional to absolute concentration of the selected gas in the flowing gas stream corresponding to said sensor.

4. The method of claim 3, wherein first and second amplifiers respectively connected to said first and second sensors are provided, to obtain signals proportional to absolute concentrations of the selected gas in each of said first and second flowing gas streams.

* * * * *